United States Patent [19]

Kimura et al.

[11] Patent Number: 4,493,730
[45] Date of Patent: Jan. 15, 1985

[54] PHENOXYPYRIDINE USEFUL AS A HERBICIDE

[75] Inventors: Fumio Kimura; Takahiro Haga, both of Shiga, Japan

[73] Assignee: Ishihara Sangyo Kaisha, Ltd., Osaka, Japan

[21] Appl. No.: 416,744

[22] Filed: Sep. 10, 1982

[51] Int. Cl.³ .................. A01N 43/40; C07D 213/61; C07D 213/64

[52] U.S. Cl. .................................... 71/94; 546/288; 546/296; 546/297

[58] Field of Search .................. 546/288, 296, 297; 71/94; 260/156

[56] References Cited

U.S. PATENT DOCUMENTS 4,076,741  2/1978  Bayer et al. .................... 260/465 F
4,235,621  11/1980  Nishiyama et al. .................. 71/94

*Primary Examiner*—Alan L. Rotman
*Attorney, Agent, or Firm*—Sughrue, Mion, Zinn, Macpeak and Seas

[57] ABSTRACT

A phenoxypyridine compound represented by the formula:

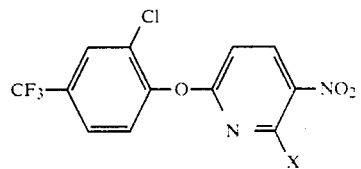

wherein X represents a hydrogen atom, an alkyl group, an alkoxy group, an amino group, a cyano group, a hydroxy group, a halogen atom, or a 2-chloro-4-trifluoromethylphenoxy group, which compound is useful as a herbicide or an intermediate for agricultural chemicals, is disclosed.

14 Claims, No Drawings

PHENOXYPYRIDINE USEFUL AS A HERBICIDE

FIELD OF THE INVENTION

This invention relates to a phenoxypyridine compound, and a herbicidal composition containing the same as an active ingredient.

BACKGROUND OF THE INVENTION

U.S. Pat. No. 3,429,689 teaches that certain phenoxypyridine compounds are useful as an active ingredient of an agent for combating harmful living things. This invention was made based on the finding that specific phenoxypyridines which are not described in the above-cited U.S. Patent have excellent properties especially as an active ingredient of a herbicide.

SUMMARY OF THE INVENTION

An object of this invention is to provide a novel phenoxypyridine compound represented by the formula (I):

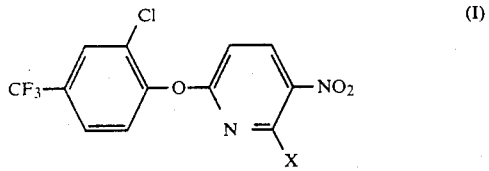

wherein X represents a hydrogen atom, an alkyl group, an alkoxy group, an amino group, a cyano group, a hydroxy group, a halogen atom, or a 2-chloro-4-trifluoromethylphenoxy group.

Another object of this invention is to provide a herbicidal composition comprising a herbicidally effective amount of at least one compound of the formula (I) as an active ingredient and agriculturally acceptable adjuvants.

DETAILED DESCRIPTION OF THE INVENTION

In the above-described definition of the formula (I), suitable examples of the halogen atom which can be used include a fluorine atom, a chlorine atom, a bromine atom, and an iodine atom; and suitable examples of the alkyl moiety in the alkyl group or alkoxy group include those having 1 to 4 carbon atoms such as a methyl group, an ethyl group, a propyl group, and a butyl group.

The phenoxypyridine compound of the formula (I) can generally be prepared in a manner as illustrated below.

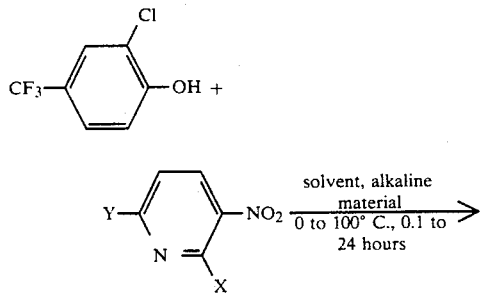

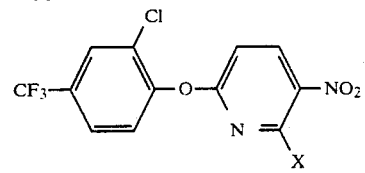

In the above-described reaction scheme, X is the same as defined above; and Y represents a halogen atom such as a chlorine atom, a bromine atom, and an iodine atom, with the chlorine atom being preferred from the industrial viewpoint. Suitable examples of the alkaline material which can be used include alkali metal hydroxides such as sodium hydroxide and potassium hydroxide; alkali metal carbonates such as sodium carbonate and potassium carbonate; and tertiary amines such as triethylamine. These alkaline materials can be added to the reaction system as they are or in a form of an aqueous solution thereof. A suitable amount of the alkaline material which is added is generally 1.0 to 5.0 moles, preferably 1.0 to 2.0 moles, per mole of the halogenated nitropyridine. Suitable examples of the solvent which can be used are aprotic polar solvents such as dimethylformamide, dimethyl sulfoxide, dimethylacetamide, N-methyl-2-pyrrolidone, hexamethylphosphoramide, and sulfolane. A suitable amount of the solvent used is generally 1 to 30 ml, preferably 3 to 10 ml, per milliliter of the halogenated nitropyridine.

In the above-described reaction, it is general and advantageous from the industrial viewpoint that substantially equimolar amounts of the halogenated nitropyridine and 2-chloro-4-trifluoromethylphenol are used.

Compounds which are obtained in the above-described manner may further be converted into other compounds of this invention by a conventional method, if desired.

The phenoxypyridine compound of the formula (I) of this invention is also useful as an intermediate in the preparation of agricultural chemicals.

Some specific examples of preparing the compounds of this invention are shown below.

PREPARATION EXAMPLE 1

Preparation of 3-Nitro-6-(2-chloro-4-trifluoromethylphenoxy)pyridine 7.6 g of anhydrous sodium carbonate and 9.8 g of 2-chloro-4-trifluoromethylphenol were added to 20 ml of dimethyl sulfoxide, and a solution having 7.9 g of 2-chloro-5-nitropyridine dissolved in 10 ml of dimethyl sulfoxide was added dropwise thereto at room temperature (i.e., about 20° to 30° C.) while stirring. After completion of the dropwise addition, the mixture was allowed to react at 50° C. for 30 minutes. After completion of the reaction, the reaction product was poured into water, followed by extracting with methylene chloride. The extracted phase was washed with water and dried, and the solvent was then distilled off to obtain 13 g of a crystal. The thus obtained crystal was recrystallized from n-hexane to obtain 9.8 g of a titled compound having a melting point of 69° to 72° C.

PREPARATION EXAMPLE 2

Preparation of 2-Amino-3-nitro-6-(2-chloro-4-trifluoromethylphenoxy)pyridine 12.5 g of 2-chloro-4-trifluoromethylphenol, 10.0 g of 2-amino-3-nitro-6-chloropyridine, 10.5 g of potassium carbonate, and 200 ml of dimethyl sulfoxide were charged in a flask, and the mixture was allowed to react at 30° C. for twenty-four hours while stirring. After completion of the reaction, the reaction product was poured into water, followed by extracting with methylene chloride. The extracted phase was washed with water and dried, and the methylene chloride was distilled off under reduced pressure to obtain 14.7 g of a titled compound having a melting point of 80° to 84° C.

PREPARATION EXAMPLE 3

Preparation of 2-Hydroxy-3-nitro-6-(2-chloro-4-trifluoromethylphenoxy)pyridine 14.0 g of 2-amino-3-nitro-6-(2-chloro-4-trifluoromethylphenoxy)pyridine prepared in Preparation Example 2 was poured into 29 ml of concentrated sulfuric acid, and the mixture was heated at 60° C. Thereafter, the resulting mixture was allowed to stand for cooling, and further cooled with ice to 0° to 10° C. An aqueous solution of 4.6 g of sodium nitrite and 14 ml of water was gradually added dropwise thereto at the same temperature while stirring whereby the mixture was allowed to react. After completion of the reaction, the reaction product was poured into water, followed by subjecting to purification in the same manner as in Preparation Example 2 to obtain 10.3 g of a titled compound having a melting point of 87° to 93° C.

PREPARATION EXAMPLE 4

Preparation of 2-Chloro-3-nitro-6-(2-chloro-4-trifluoromethylphenoxy)pyridine 5.0 g of 2-hydroxy-3-nitro-6-(2-chloro-4-trifluoromethylphenoxy)pyridine prepared in Preparation Example 3, 3.55 g of thionyl chloride, and 0.2 ml of dimethylformamide were charged in a flask, and the mixture was allowed to react at 80° C. for 4 hours while stirring. After completion of the reaction, the reaction product was poured into water, followed by subjecting to purification in the same manner as in Preparation Example 2 to obtain 2.64 g of a titled compound having a melting point of 53° to 59° C.

Specific examples of the compounds of this invention which can be prepared in accordance with the above-described preparation method and Preparation Examples are listed in Table 1.

TABLE 1

[Structure: 2-chloro-4-trifluoromethylphenoxy pyridine with NO2 and X substituents]

| Compound No. | X | Physical Property (Melting Point) |
|---|---|---|
| 1 | H | 69 to 72° C. |
| 2 | —NH$_2$ | 80 to 84° C. |
| 3 | —OH | 87 to 93° C. |
| 4 | —Cl | 53 to 59° C. |
| 5 | —OCH$_3$ | 88 to 94° C. |
| 6 | —CN | 83 to 89° C. |
| 7 | —CH$_3$ | 54 to 56° C. |
| 8 | [2-chloro-4-trifluoromethylphenoxy group] | 107 to 109° C. |

The compounds of this invention have an excellent effect for controlling noxious weeds. For example, when they are applied to a paddy field, they can effectively control noxious weeds such as barnyardgrass, yellow nutsedge, toothcup, hardstem bulrush, arrowhead, water nutgrass, etc. with substantially no phytotoxicity against crops such as rice, etc. Further, when they are applied to an up-land farm, they can effectively control noxious weeds such as heartleaf cocklebur, pickly sida, black nightshade, smartweed, large crabgrass, barnyardgrass, redroot pigweed, etc. with substantially no phytotoxicity against crops such as soybean, corn, wheat, etc.

Herbicides comprising a compound of this invention as an active ingredient can be applied broadly to orchards, mulberry fields, mountains and forests, farm roads, playgrounds, factory sites, etc. in addition to paddy fields and up-land farms. The application procedure can be selected from various techniques such as soil treatment, foliar treatment and the like.

Although the compounds of this invention can be applied as they are, they are generally used in a form of emulsifiable concentrate, water miscible solution, wettable powder, dust, granule, etc. by mixing with various agriculturally acceptable adjuvants, if desired. Suitable examples of the agriculturally acceptable adjuvants which can be used include carriers such as diatomaceous earth, calcium hydroxide, calcium carbonate, talc, white carbon, kaolin, bentonite, and Jeeklite (trade name for kaolinite, produced by Jeeklite Co.); solvents such as n-hexane, toluene, xylene, solvent naphtha, ethanol, dioxane, acetone, isophorone, methyl isobutyl ketone, dimethylformamide, dimethyl sulfoxide, and water; and anionic or nonionic surface active agents such as sodium alkylsulfates, sodium alkylbenzenesulfonates, sodium ligninsulfonate, polyoxyethylene lauryl ether, polyoxyethylene alkylaryl ethers, polyoxyethylene fatty acid esters, and polyoxyethylene sorbitan fatty acid esters. The herbicidal composition of this invention usually comprises 1 to 90% by weight, preferably 1 to 70% by weight, of the active ingredient; 5 to 99% by weight preferably 25 to 99% by weight, of the carrier or solvent; and 0 to 30% by weight, preferably 1 to 20% by weight, of the surface active agent.

The herbicidal composition of this invention can also be mixed or used together with suitable agricultural chemicals such as other herbicides, insecticides, and fungicides, or mixed with agricultural agents such as fertilizers, soil conditioners, soils, and sands. Sometimes, such conjoint use brings about a better effect.

A suitable amount of the herbicide of this invention to be applied cannot be unequivocally defined as it varies depending upon the climatic conditions, the soil conditions, the form of the chemical, the time of application, the application procedure or the types of weeds to be controlled. Usually, the amount of the active ingredient is 1 to 100 g, preferably 2 to 60 g, per are.

Some typical examples of herbicidal formulations containing the compound of this invention are shown below.

FORMULATION EXAMPLE 1

| (1) | Bentonite | 58 parts by weight |
|---|---|---|
| (2) | Jeeklite | 30 parts by weight |
| (3) | Sodium Ligninsulfonate | 5 parts by weight |

These ingredients were mixed and granulated, and 7 parts by weight of Compound No. 6 of this invention which had been diluted with a suitable amount of acetone was sprayed on the granulated ingredients to form granules.

FORMULATION EXAMPLE 2

| (1) | Jeeklite | 78 parts by weight |
|---|---|---|
| (2) | Lavelin S (trade name for a sodium naphthalene sulfonate-formaldehyde condensate, produced by Daiichi Kogyo Seiyaku Co., Ltd.) | 2 parts by weight |
| (3) | Sorpol 5039 (trade name for a mixture of polyoxyethylene alkylaryl ether sulfate and fine silicon dioxide (50:50)) | 5 parts by weight |
| (4) | Carplex (trade name for a fine silicon dioxide white carbon), produced by Shionogi Seiyaku Co., Ltd.) | 15 parts by weight |

A mixture of these ingredients was mixed with Compound No. 4 of this invention in a ratio of 4:1 to form a wettable powder.

FORMULATION EXAMPLE 3

| (1) | Compound No. 5 of this invention | 20 parts by weight |
|---|---|---|
| (2) | Xylene | 60 parts by weight |
| (3) | Sorpol 2806B (trade name for a mixture of polyoxyethylene phenyl phenol derivative, polyoxyethylene alkylaryl ether, polyoxyethylene sorbitan alkylate, and alkylaryl sulfonate, produced by Toho Chemical Co., Ltd.) | 20 parts by weight |

These ingredients were mixed and dissolved to form an emulsifiable concentrate.

The herbicidal activity testing of the compound of this invention and results obtained are shown below.

TEST EXAMPLE 1

Each 1/5,000 are (1/50 m$^2$) pot was filled with a paddy soil, and the soil was supersaturated with water. Predetermined amounts of seeds of edible barnyardgrass and hardstem bulrush were sown in the pot. The test plants were sprout in a green house and then grown in the flooded condition of a depth of 3 cm. An aqueous dispersion of each compound shown in Table 2 below in an amount of 20 g per are was poured into the pot. Twenty days after the treatment, the degree of growth inhibition of the plants was visually evaluated. The results obtained are also shown in Table 2. The degree of growth inhibition shown in Table 2 was evaluated on a scale of 5 grades in which 5 indicates that the growth was completely inhibited, and 1 indicates no inhibition, i.e., no apparent difference between treated plants and untreated plants.

TABLE 2

| | Degree of Growth Inhibition | |
|---|---|---|
| Active Ingredient | Edible Barnyardgrass | Hardstem Bulrush |
| Invention: | | |
| 3-Nitro-6-(2-chloro-4-trifluoromethylphenoxy)pyridine | 5 | 5 |
| 2-Chloro-3-nitro-6-(2-chloro-4-trifluoromethylphenoxy)-pyridine | 5 | 3 |
| 2-Methoxy-3-nitro-6-(2-chloro-4-trifluoromethylphenoxy)-pyridine | 5 | 5 |
| Comparison: | | |
| 2-(4-Nitrophenoxy)pyridine | 1 | 1 |
| 2-(2,4-Dichlorophenoxy)-5-nitropyridine | 2 | 1 |

TEST EXAMPLE 2

In a green house, each 1/5,000 are (1/50 m$^2$) pot was charged with a soil to provide an up-land condition. Predetermined amounts of seeds of soybean, corn, rice and various weeds were sown in the pot. Next day, a predetermined amount of an aqueous dispersion of each compound shown in Table 3 below was sprayed on the plants. Twenty-five days after the spraying, the degree of growth inhibition of the plants was visually evaluated. The results obtained are also shown in Table 3. The degree of growth inhibition shown in Table 3 was evaluated on a scale of 10 grades in which 10 indicates that the growth was completely inhibited, and 1 indicates no inhibition, i.e., no apparent difference between treated plants and untreated plants.

TABLE 3

| Active Ingredient | Amount of Active Ingredient (g/are) | Degree of Growth Inhibition | | | | | | |
|---|---|---|---|---|---|---|---|---|
| | | A | B | C | D | E | F | G |
| Invention: | | | | | | | | |
| 3-Nitro-6-(2-chloro-4-trifluoromethylphenoxy)pyridine | 40 | 1 | 1 | 1 | 10 | 10 | 10 | 10 |
| | 20 | 1 | 1 | 1 | 6 | 10 | 10 | 10 |
| 2-Chloro-3-nitro-6-(2-chloro-4-trifluoromethylphenoxy)pyridine | 40 | 1 | 1 | 1 | 10 | 10 | 10 | 10 |
| | 20 | 1 | 1 | 1 | 9 | 10 | 9 | 9 |

TABLE 3-continued

| Active Ingredient | Amount of Active Ingredient (g/are) | Degree of Growth Inhibition | | | | | | |
|---|---|---|---|---|---|---|---|---|
| | | A | B | C | D | E | F | G |
| 2-Methoxy-3-nitro-6-(2-chloro-4-trifluoromethyl-phenoxy)pyridine | 40 | 1 | 1 | 1 | 10 | 10 | 10 | 10 |
| | 20 | 1 | 1 | 2 | 10 | 10 | 10 | 10 |
| 2-Methyl-3-nitro-6-(2-chloro-4-trifluoromethylphenoxy)-pyridine | 40 | 1 | 1 | 2 | 10 | 10 | 10 | 10 |
| | 20 | 1 | 1 | 1 | 8 | 9 | 9 | 9 |
| 2,6-Bis-(2-chloro-4-trifluoro-methylphenoxy)-3-nitropyridine | 40 | 1 | 1 | 1 | 8 | 8 | 8 | 9 |
| | 20 | 1 | 1 | 1 | 6 | 7 | 7 | 8 |
| 2-Cyano-3-nitro-6-(2-chloro-4-trifluoromethylphenoxy)-pyridine | 40 | 1 | 1 | 1 | 1 | 10 | 9 | 9 |
| | 20 | 1 | 1 | 1 | 1 | 9 | 8 | 9 |
| Comparison: | | | | | | | | |
| 2-(4-Nitrophenoxy)-pyridine | 40 | 1 | 1 | 1 | 1 | 1 | 1 | 1 |
| | 20 | 1 | 1 | 1 | 1 | 1 | 1 | 1 |
| 2-(2,4-Dichlorophenoxy)-5-nitropyridine | 20 | 1 | 1 | 1 | 2 | 3 | 2 | 1 |

A: soybean
B: corn
C: rice
D: barnyardgrass
E: redroot pigweed
F: black nightshade
G: smartweed

TEST EXAMPLE 3

In a green house, each 1/5,000 are (1/50 m$^2$) flat was charged with a soil to provide an up-land condition. Predetermined amounts of seeds of corn and various weeds were sown in the flat. When each of corn and weeds reached a predetermined leaf stage, a predetermined amount of an aqueous dispersion of each compound shown in Table 4 below was foliarly sprayed on the plants. Twenty days after the spraying, the degree of growth inhibition of the plants was visually evaluated on the same scale as in Test Example 2. The results obtained are also shown in Table 4.

TABLE 4

| Active Ingredient | Amount of Active Ingredient (g/are) | Degree of Growth Inhibition | | | | |
|---|---|---|---|---|---|---|
| | | H | I | J | K | L | M |
| 2-Chloro-3-nitro-6-(2-chloro-4-trifluoromethyl-phenoxy)pyridine | 5 | 1 | 10 | 10 | 10 | 10 | 10 |
| | 2.5 | 1 | 10 | 10 | 10 | 10 | 10 |
| 2-Methoxy-3-nitro-6-(2-chloro-4-trifluoromethyl-phenoxy)pyridine | 5 | 1 | — | 7 | 10 | 10 | — |
| | 2.5 | 1 | 8 | 9 | 10 | 10 | 8 |
| 2-Cyano-3-nitro-6-(2-chloro-4-trifluoromethyl-phenoxy)pyridine | 10 | 2 | 10 | 10 | 10 | 10 | 10 |
| | 5 | 1 | 10 | 9 | 10 | 10 | 10 |

H: corn (4-leaf stage)
I: heartleaf cocklebur (2-leaf stage)
J: morning-glory (1-leaf stage)
K: redroot pigweed (1-leaf stage)
L: smartweed (2-leaf stage)
M: black nightshade (1-leaf stage)

While the invention has been described in detail and with reference to specific embodiments thereof, it will be apparent to one skilled in the art that various changes and modifications can be made therein without departing from the spirit and scope thereof.

What is claimed is:

1. A phenoxypyridine compound represented by the formula (I):

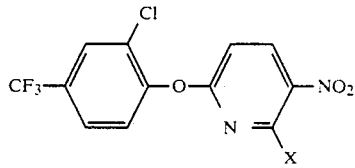

wherein X represets hydrogen atom, alkyl group having 1 to 4 carbon atoms, alkoxy group having 1 to 4 carbon atoms, amino group, cyano group, hydroxy group, fluorine atom, chlorine atom, bromine atom, iodine atom, or 2-chloro-4-trifluoromethylphenoxy group.

2. A compound according to claim 1, wherein X represents hydrogen atom.

3. A compound according to claim 1, wherein X represents alkyl group having 1 to 4 carbon atoms.

4. A compound according to claim 1, wherein X represents alkoxy group having 1 to 4 carbon atoms.

5. A compound according to claim 1, wherein X represents cyano group.

6. A compound according to claim 1, wherein X represents fluorine atom, chlorine atom, bromine atom, or iodine atom.

7. A compound according to claim 1, wherein X represents 2-chloro-4-trifluoromethylphenoxy group.

8. A herbicidal composition comprising an effective amount of a phenoxypyridine compound represented by the formula (I):

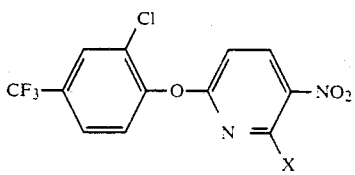

wherein X represents hydrogen atom, alkyl group having 1 to 4 carbon atoms, alkoxy group having 1 to 4 carbon atoms, amino group, cyano group, hydroxy group, fluorine atom, chlorine atom, bromine atom, iodine atom, or 2-chloro-4-trifluoromethylphenoxy group, as an active ingredient and an agriculturally acceptable adjuvant.

9. A herbicidal composition according to claim 8, wherein X represents hydrogen atom.

10. A herbicidal composition according to claim 8, wherein X represents alkyl group having 1 to 4 carbon atoms.

11. A herbicidal composition according to claim 8, wherein X represents alkoxy group having 1 to 4 carbon atoms.

12. A herbicidal composition according to claim 8, wherein X represents cyano group.

13. A herbicidal composition according to claim 8, wherein X respesents fluorine atom, chlorine atom, bromine atom, or iodine atom.

14. A herbicidal composition according to claim 8, wherein X represents 2-chloro-4-trifluoromethylphenoxy group.

* * * * *